United States Patent [19]

Workman

[11]  4,374,853

[45]  Feb. 22, 1983

[54] METHOD FOR CONTROLLING ECTOPARASITES

[76] Inventor: Lester J. Workman, P.O. Box 5547, Sarasota, Fla. 33579

[21] Appl. No.: 249,696

[22] Filed: Mar. 31, 1981

[51] Int. Cl.³ .................. A01N 41/02; A61K 31/255; A61K 31/14
[52] U.S. Cl. ..................................... 424/303; 424/329
[58] Field of Search ........................ 424/303, 329, 148

[56]  References Cited

U.S. PATENT DOCUMENTS

| | | | |
|---|---|---|---|
| 2,666,728 | 1/1954 | Smith | 424/329 |
| 2,739,097 | 3/1956 | Ward | 424/329 |
| 2,771,395 | 11/1956 | Mehaffey | 424/329 |
| 3,093,591 | 6/1963 | Freese | 424/329 |
| 3,634,264 | 1/1972 | Pence | 424/329 |
| 4,235,898 | 11/1980 | Watanabe et al. | 424/70 |

OTHER PUBLICATIONS

Boczek et al., Chem. Abst., vol. 69, (1968), p. 84, 543 Q.

Primary Examiner—Sam Rosen
Attorney, Agent, or Firm—Cushman, Darby & Cushman

[57]  ABSTRACT

Ectoparasites, such as fleas, on warm blooded animals, i.e. dogs and cats, are controlled by applying to the animal an insect killing composition composed essentially of an aqueous antiseptic liquid containing at least one compatible surface active agent and alcohol according to the disclosed invention. The insect controlling composition, which is typically a liquid, is applied to the animal's body while the fur is still dry. The composition is rubbed into the fur until lathering begins then it is washed thoroughly from the animal's body and dried. Fleas in dogs and cats are effectively controlled by this procedure.

9 Claims, No Drawings

METHOD FOR CONTROLLING ECTOPARASITES

BACKGROUND OF THE INVENTION

This invention relates to novel insect killing compositions for the control of ectoparasites on animals and to methods for using the compositions. More particularly, the invention relates to the control of fleas on warm blooded animals such as dogs and cats, by application of an insecticidal composition, conveniently in the form of a shampoo, directly to the animal's body.

Various washes and shampoos have been proposed in the art for controlling fleas on cats and dogs. However, there have been several untoward effects caused by such products. These include allergic sensitivity reactions evidenced by the animal's skin and/or fur and difficulty in use, i.e. long "soak" times were required for lack of effectiveness of such products. More recently the use of pet collars, in which an insecticide gas generating composition is included, have been widely adopted. These types of products also suffer from certain disadvantages. For instance, pet collars composed of the insecticide dimethyl 2,2-dichlorovinyl phosphate, commonly known as DDVP, have been widely used for the purpose of controlling fleas on dogs and cats. DDVP has been reported in the literature to have an objectionable depressing effect on the plasma and red cell cholinesterase. This is particularly acute at high concentrations which are produced during the first few days after a collar has been applied to the neck of the animal. Additionally, local skin irritation has occurred at the site of the collar especially when the collar is first placed on the animal.

Despite these proposals and numerous commercially available products, a need exists in the art for providing a safe yet fully effective composition for treating animals such as dogs and cats for fleas.

DESCRIPTION OF THE INVENTION

I have discovered and hereby disclose compositions which are generally useful in controlling ectoparasites which infest domestic animals. These compositions are particularly useful against fleas and ticks. Also included within my invention is a novel method of treating animals such as dogs or cats for fleas which involves applying the compositions of my invention to the insect-infested animal for a period of time sufficient to eradicate or control the insects infesting the involved animal.

The compositions of my invention contain at least two essential ingredients. These include an aqueous solution of an alcohol, typically ethanol, together with essential oils and flavorings and, as the second component, a surface active agent which is compatible with the antiseptic solution component and provides the necessary wetting action for the compositions.

My invention also includes a method of controlling or eradicating pest insects harbored by warm blooded animals, particularly controlling fleas on dogs and cats, by applying the compositions of my invention directly to the infested animal.

More specifically the method of my invention for controlling or eradicating ectoparasites on warm blooded animals comprises (1) applying to the infested animal an insecticidally effective amount of a composition composed of an aqueous alcohol solution containing at least one compatible surface active agent incorporated herein, then (2) allowing the thus applied composition to remain in contact with the animal's skin and fur for a period of time sufficient to at least control and preferably eradicate the parasites contained thereon, and thereafter (3) removing the composition. Preferably the composition is composed of an aqueous ethanol solution together with an anionic surface active agent and is in the form of a shampoo. When applied as in step (1) the shampoo is lathered then rinsed off of the animal's skin and fur. Typically fleas are the ectoparasites and cats and dogs are the animals involved.

In particular my novel method of controlling fleas on cats and dogs comprises the sequential steps of: (a) applying to the fur and skin of the flea infested cat or dog a flea-controlling amount of an aqueous solution of ethanol to surfactant in the ratio of about 2:1; (b) allowing the thus-applied solution to remain in contact with the cat or dog's skin and fur for a period of time sufficient to eradicate substantially all of the fleas contained therein and thereon; and (c) rinsing the applied solution from the fur and skin.

Preferably the solution remains on the fur and skin for a period of time of from about 30 seconds to about 5 minutes and the surfactant is an anionic sulfonated ester surfactant.

The compositions of my invention include at least an aqueous alcohol solution, at least one surfactant compound and optionally colorants, perfumes, stabilizers and the like. The aqueous alcohol solution preferably contains from about 4 to about 30% by volume of alcohol, typically ethanol. Also inorganic salts or acids may be included, for example sodium borate or boric acid. Of such solutions I have found various preparations previously used as mouth washes quite useful when combined with the appropriate surfactant. Of the numerous available reference texts available mention is made of Remington's Pharmaceutical Sciences, Edition XIII, Mack Publishing Company (1965) particularly pages 1229 and 1240, the disclosure of which is relied upon and incorporated herein by reference. Two particular preparations, N.F. Mouthwash (contents of same given in the Example, below) and N.F. Antiseptic Solution (ingredients given below), are preferred.

| | |
|---|---|
| potassium bicarbonate | 20 g |
| sodium borate | 20 g |
| thymol | 0.5 g |
| eucalyptol | 1 ml |
| methyl salicylate | 0.5 g |
| amaranth solution (optional) | 14 ml |
| ethanol | 50 ml |
| glycerin | 100 ml |
| purified water q.s. | 1,000 ml |

This preparation is also known as N.F. Mouthwash when the amaranth solution is included.

From the above listing it will be apparent that there are numerous similar solutions which may be employed, together with a suitable surfactant or surfactant system, and assessed on a case-by-case basis.

As the surfactant component of the insecticidal compositions of the present invention one can use one or more of many suitable synthetic detergent active compounds which are readily available in commerce and described in the literature, for example in "Surface Active Agents and Detergents", Volumes 1 and 2 by Schwartz, Perry and Berch. Generally stated, the surface active component may include a synthetic anionic, nonionic, amphoteric or zwitterionic compound or mixtures of two or more of these compounds. Preferably cationic, anionic and/or nonionic compounds are used.

Hair shampoos represent a class of potential surface-active agents, particularly those described in "Modern Cosmeticology", Wilkinson et al, Leonard Hill, London (1968) at pages 359–362, the disclosure of which is hereby incorporated by reference. A preferred surface active material is Deceresol Surfactant OT available from American Cyanamid, Organic Chemicals Division. It is identified in McCutcheon's Detergents and Emulsifiers (page 2977) as a sulfonated ester-type compound in liquid form and is characterized as being anionic in type. Also the sodium and calcium salts of dioctyl sulfosuccinate, items 3287 and 3288, *The Merck Index* (1976), may be considered. Thus from the above grouping a selection will be made of a pharmaceutically appropriate and insecticidally effective surface active agent which when mixed with the aqueous alcohol solution provides an effective yet non-irritating insecticidal composition.

It will be understood that while my invention has been described with respect to eradicating or controlling insect infestations in animals, particularly fleas on cats and dogs, there are numerous other applications to which the compositions of my invention may be put. Also in explaining my invention reference is herein made to various specific procedures and methods for accomplishing the desired result of eradicating or controlling ectoparasites on warm blooded animals. It will be understood that other procedures and methods are contemplated herein for the desired insect control in addition to those specifically described, utilizing the compositions of my invention.

My invention will now be further illustrated with reference to the following example.

EXAMPLE

A topically applied formulation with shampooing properties was made according to the following procedure:

A solution was prepared identified as "NF Antiseptic Solution" according to procedures described in the National Formulary

| boric acid | 25 g |
|---|---|
| thymol | 0.5 g |
| chlorothymol | 0.5 g |
| menthol | 0.5 g |
| eucalyptol | 0.1 ml |
| methyl salicylate | 0.2 ml |
| thyme oil | 0.01 ml |
| ethanol | 300 ml |
| purified water, q.s. to make 1,000 ml | |

The procedure employed was as described in Remington's Pharmaceutical Sciences (1965), page 1129. Compositons so prepared usually contain from 26 to 29% by volume of ethanol therein.

To 828 ml (28 oz.) of the antiseptic solution prepared as above 118 ml (4 oz.) of Decerosol OT (75% aqueous solution) was added and the mixture agitated to insure proper mixing. A light amber, clear solution resulted.

A neutered female standard Schnauzer infested with numerous fleas was treated as follows: One volume of the surfactant/antiseptic solution as prepared above was diluted with three volumes of warm tap water to form a 25% V/V solution. The solution was applied to the animal with a sponge in an amount sufficient to thoroughly wet the animal's fur. The applied solution was allowed to remain on the animal and the fur rubbed until lathering occurred. The composition was rinsed off with warm tap water until the rinse water was clear. The animal was then dried.

A gross visual examination shortly after the animal was dry and again two weeks later indicated no fleas or flea residue.

What is claimed is:

1. A method of killing ectoparasites on warm blooded animals comprising: (1) applying to said animal an insecticidally effective amount of a composition consisting essentially of an aqueous alcohol solution containing at least one compatible, insecticidally effective surface active wetting agent incorporated therein, (2) allowing the thus applied composition to remain in contact with the animal's skin and fur for a period of time sufficient to kill the parasites contained therein, and thereafter (3) removing the composition and killed parasites.

2. The method of claim 1, wherein said composition is composed of an aqueous ethanol solution together with an anionic surface active wetting agent.

3. The method of claim 1 or 2 wherein said composition is a shampoo.

4. The method of claim 3, wherein after said composition is applied in step (1) the shampoo is lathered prior to rinsing off of the animal's skin and fur.

5. The method of claim 1 or 2 wherein fleas are the ectoparasites and cats and dogs are the animals.

6. The method of claim 1 wherein the solution remains on the fur and skin for from about 30 seconds to about 5 minutes.

7. The method according to claim 1 or 4 wherein the surface active wetting agent is an anionic sulfonated ester surfactant.

8. A method of killing fleas on cats and dogs comprising the sequential steps of:
   (a) applying to the fur and skin of the flea-infested cat or dog a flea-killing amount of an aqueous-alcohol solution consisting essentially of at least one insecticidally effective sulfonated ester anionic surfactant wherein the ethanol to surfactant ratio in the solution is about 2:1;
   (b) allowing the thus-applied solution to remain in contact with the cat or dog's skin and fur for a period of time to kill substantially all of the fleas contained therein and thereon; and
   (c) rinsing the applied solution and the killed fleas from the animal's fur and skin.

9. A method of killing fleas on cats and dogs comprising the sequential steps of:
   (a) applying to the fur and skin of the flea-infested cat or dog a flea-controlling amount of an aqueous solution of an insecticidally effective anionic sulfonated ester surfactant and ethanol, wherein the ratio of ethanol to surfactant is about 2:1;
   (b) allowing the thus-applied solution to remain in contact with the cat or dog's skin and fur for a period of time of from about 30 seconds to about 5 minutes sufficient to kill substantially all of the fleas contained therein and thereon; and
   (c) rinsing the applied solution and killed fleas from the animal's fur and skin.

* * * * *